United States Patent
Yang et al.

(10) Patent No.: US 7,566,726 B2
(45) Date of Patent: Jul. 28, 2009

(54) 3,3-DISUBSTITUTED TETRAHYDROPYRANYL CYCLOPENTYL AMIDE MODULATORS OF CHEMOKINE RECEPTOR ACTIVITY

(75) Inventors: Lihu Yang, Edison, NJ (US); Sander G. Mills, Scotch Plains, NJ (US); Kothandaraman Shankaran, Kendall Park, NJ (US)

(73) Assignee: Merck & Co. Inc., Rahway, NJ (US)

( * ) Notice: Subject to any disclaimer, the term of this patent is extended or adjusted under 35 U.S.C. 154(b) by 285 days.

(21) Appl. No.: 11/587,448

(22) PCT Filed: Apr. 22, 2005

(86) PCT No.: PCT/US2005/013752

§ 371 (c)(1),
(2), (4) Date: Oct. 24, 2006

(87) PCT Pub. No.: WO2005/105092

PCT Pub. Date: Nov. 10, 2005

(65) Prior Publication Data

US 2008/0021057 A1    Jan. 24, 2008

Related U.S. Application Data

(60) Provisional application No. 60/566,012, filed on Apr. 28, 2004.

(51) Int. Cl.
*C07D 217/02* (2006.01)
*C07D 471/02* (2006.01)
*A61K 31/4375* (2006.01)

(52) U.S. Cl. ........................ 514/300; 514/307; 546/122; 546/146

(58) Field of Classification Search ........................ None
See application file for complete search history.

(56) References Cited

FOREIGN PATENT DOCUMENTS

| JP | 09-104674 | 6/1996 |
|---|---|---|
| WO | WO 03092586 | 4/2003 |
| WO | WO 03093231 | 4/2003 |
| WO | WO 03093266 | 4/2003 |
| WO | WO 2004110376 | 6/2004 |

*Primary Examiner*—Zinna N Davis
(74) *Attorney, Agent, or Firm*—James L. McGinnis; Mark R. Daniel

(57) ABSTRACT

Compounds of Formula I:

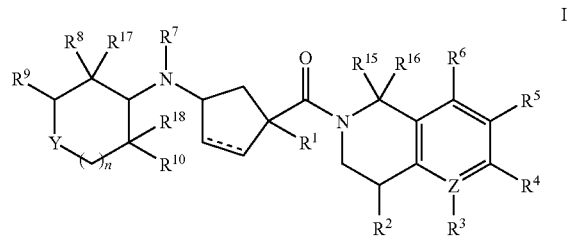

(wherein n, $R^1$, $R^2$, $R^3$, $R^4$, $R^5$, $R^6$, $R^7$, $R^8$, $R^9$, $R^{10}$, $R^{15}$, $R^{16}$, $R^{17}$, $R^{18}$, Y and Z are defined herein) which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

14 Claims, No Drawings

3,3-DISUBSTITUTED TETRAHYDROPYRANYL CYCLOPENTYL AMIDE MODULATORS OF CHEMOKINE RECEPTOR ACTIVITY

RELATED APPLICATION DATA

This is a National filing under 35 USC 371 of PCT/US2005/013752, filed Apr. 22, 2005, which claims priority from U.S. Ser. No. 60/566,012, filed Apr. 28, 2004.

BACKGROUND OF THE INVENTION

The chemokines are a family of small (70-120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, Cytokine, 3, 165-183 (1991) and Murphy, Rev. Immun., 12, 593-633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, monocytes, T-cells, eosinophils and basophils (Deng, et al., Nature, 381, 661-666 (1996)).

The chemokines are secreted by a wide variety of cell types and bind to specific G-protein coupled receptors (GPCRs) (reviewed in Horuk, Trends Pharm. Sci., 15, 159-165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., J. Biol. Chem., 270, 22123-22128 (1995); Beote, et al, Cell, 72, 415-425 (1993)); CCR-2A and CCR-2B (or "CKR-2A"/"CKR-2A"or "CC-CKR-2A"/"CC-CKR-2A") [MCP-1, MCP-2, MCP-3, MCP-4]; CCR-3 (or "CKR-3" or "CC-CKR-3") [Eotaxin, Eotaxin 2, RANTES, MCP-2, MCP-3] (Rollins, et al., Blood, 90, 908-928 (1997)); CCR-4 (or "CKR-4" or "CC-CKR-4") [MIP-1β RANTES, MCP-1] (Rollins, et al., Blood, 90, 908-928 (1997)); CCR-5 (or "CKR-5" or "CC-CKR-5") [MIP-1α RANTES, MIP-1β] (Sanson, et al., Biochemistry, 35, 3362-3367 (1996)); and the Duffy blood-group antigen [RANTES, MCP-1] (Chaudhun, et al., J. Biol. Chem., 269, 7835-7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., Arthritis & Rheumatism, 42, 989-992 (1999)). A review of the role of eosinophils in allergic inflammation is provided by Kita, H., et al., J. Exp. Med. 183, 2421-2426 (1996). A general review of the role of chemokines in allergic inflammation is provided by Lustger, A. D., New England J. Med., 338(7), 426-445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and Listeria monocytogenes infection (Lu et al., J. Exp. Med., 187, 601-608 (1998); Kurihara et al. J. Exp. Med., 186, 1757-1762 (1997); Boring et al. J. Clin. Invest., 100, 2552-2561 (1997); Kuziel et al. Proc. Natl. Acad. Sci., 94, 12053-12058 (1997)). Furthermore, these animals show reduced monocyte infiltration into granulomatous lesions induced by the injection of schistosomal or mycobacterial antigens (Boring et al. J. Clin. Invest., 100, 2552-2561 (1997); Warmington et al. Am J. Path., 154, 1407-1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases.

Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1-/- or CCR2-/- mice backcrossed to APO-E-/-, LDL-R-/- or Apo B transgenic mice maintained on high fat diets (Boring et al. Nature, 394, 894-897 (1998); Gosling et al. J. Clin. Invest., 103, 773-778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is further directed to compounds of Formula I:

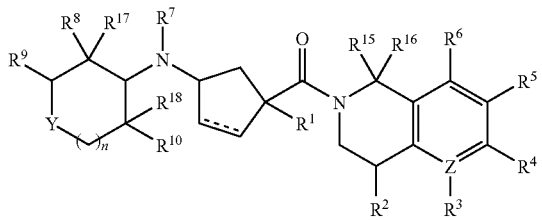

(wherein n, $R^1$, $R^2$, $R^3$, $R^4$, $R^5$, $R^6$, $R^7$, $R^8$, $R^9$, $R^{10}$, $R^{15}$, $R^{16}$, $R^{17}$, $R^{18}$, Y and Z are as defined herein) which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of Formula I:

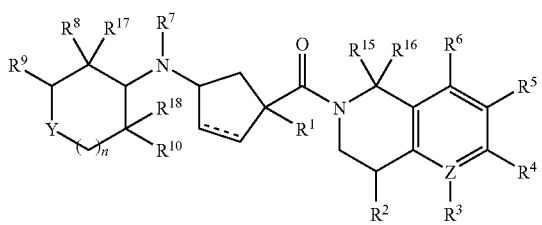

wherein:
Y is selected from: —O—, —$NR^{12}$—, —S—, —SO—, —$SO_2$—, —$CR^{12}R^{12}$—, —$NSO_2R^{14}$—, —$NCOR^{13}$—, —$CR^{12}COR^{11}$—, —$CR^{12}OCOR^{13}$—, and —CO—;
Z is C or N;
$R^1$ is selected from: hydrogen, —$SO_2R^{14}$, $C_{0-3}$alkyl-S(O)$R^{14}$, —$SO_2NR^{12}R^{12}$, —$C_{1-6}$alkyl, —$C_{0-6}$alkyl-O—$C_{1-6}$ alkyl, —$C_{0-6}$alkyl-S—$C_{1-6}$alkyl, —($C_{0-6}$alkyl)-($C_{3-7}$cycloalkyl)-($C_{0-6}$alkyl), hydroxy, heterocycle, —CN, —$NR^{12}R^{12}$, —$NR^{12}COR^{13}$, —$NR^{12}SO_2R^{14}$, —$COR^{11}$, —$CONR^{12}R^{12}$, and phenyl,
where said alkyl and said cycloalkyl are unsubstituted or substituted with 1-7 substituents independently selected from: halo, hydroxy, —O—$C_{1-3}$alkyl, trifluoromethyl, $C_{1-3}$alkyl, —O—$C_{1-3}$alkyl, —$COR^{11}$, —$SO_2R^{14}$, —$NR^{12}COR^{13}$, —$NR^{12}SO_2R^{14}$, -heterocycle, =O connected to R1 via a double bond, and —CN,
where said phenyl and said heterocycle are unsubstituted or substituted with 1-3 substituents independently selected from: halo, hydroxy, $COR^{11}$, $C_{1-3}$alkyl, $C_{1-3}$alkoxy and trifluoromethyl;
$R^2$ is selected from: hydrogen, hydroxy, halo, $C_{1-3}$alkyl unsubstituted or substituted with 1-6 substituents independently selected from fluoro and hydroxy, —$NR^{12}R^{12}$, —$COR^{11}$, —$CONR^{12}R^{12}$, —$NR^{12}COR^{13}$, —$OCONR^{12}R^{12}$, —$NR^{12}CONR^{12}R^{12}$, -heterocycle, —CN, —$NR^{12}$—$SO_2$—$NR^{12}R^{12}$, —$NR^{12}$—$SO_2$—$R^{14}$, —$SO_2$—$NR^{12}R^{12}$ and =O, where $R^2$ is connected to the ring via a double bond;
$R^3$ is selected from: hydrogen, $C_{1-3}$alkyl, unsubstituted or substituted with 1-3 fluoro, —O—$C_{1-3}$alkyl unsubstituted or substituted with 1-3 fluoro, hydroxy, chloro, fluoro, bromo, phenyl, heterocycle, when Z is C, or
$R^3$ is O or is absent, when Z is N;
$R^4$ is selected from: hydrogen, $C_{1-3}$alkyl, unsubstituted or substituted with 1-3 fluoro, —O—$C_{1-3}$alkyl optionally substituted with 1-3 fluoro, hydroxy, chloro, fluoro, bromo, phenyl and heterocycle;
$R^5$ is selected from: $C_{1-6}$alkyl unsubstituted or substituted with one or more of 1-6 fluoro and hydroxyl, —O—$C_{1-6}$ alkyl unsubstituted or substituted with 1-6 fluoro, —CO—$C_{1-6}$alkyl unsubstituted or substituted with 1-6 fluoro, —S—$C_{1-6}$alkyl unsubstituted or substituted with 1-6 fluoro, -pyridyl unsubstituted or substituted with one or more of halo, trifluoromethyl, $C_{1-4}$alkyl and $COR^{11}$, fluoro, chloro, bromo, —$C_{4-6}$cycloalkyl, —O—$C_{4-6}$cycloalkyl, phenyl unsubstituted or substituted with one or more of halo, trifluoromethyl, $C_{1-4}$alkyl and $COR^{11}$, —O-phenyl unsubstituted or substituted with one or more of halo, trifluoromethyl, $C_{1-4}$alkyl and $COR^{11}$, —$C_{3-6}$cycloalkyl unsubstituted or substituted with 1-6 fluoro, —O—$C_{3-6}$cycloalkyl unsubstituted or substituted with 1-6 fluoro, -heterocycle, —CN and —$COR^{11}$;
$R^6$ is selected from: hydrogen, $C_{1-3}$alkyl unsubstituted or substituted with 1-3 fluoro, —O—$C_{1-3}$alkyl unsubstituted or substituted with 1-3 fluoro, hydroxy, chloro, fluoro, bromo, phenyl and heterocycle;
$R^7$ is selected from: hydrogen and $C_{1-6}$alkyl unsubstituted or substituted with 1-3 substituents independently selected from halo, hydroxy, —$CO_2H$, —$CO_2C_{1-6}$alkyl and —O—$C_{1-3}$alkyl;
$R^8$ is selected from: $C_{1-6}$alkyl unsubstituted or substituted with 1-6 substituents where the substituents are chosen from the group: fluoro, $C_{1-3}$alkoxy, hydroxyl and —$COR^{11}$, fluoro, —O—$C_{1-3}$alkyl unsubstituted or substituted with 1-3 fluoro, $C_{3-6}$cycloalkyl, —O—$C_{3-6}$cycloalkyl, hydroxy, —$COR^{11}$, —$OCOR^{13}$ and =O, where the oxygen is connected to the ring via a double bond,
or $R^7$ and $R^8$ together are $C_{2-4}$alkyl or $C_{0-2}$alkyl-O—$C_{1-3}$ alkyl, forming a 5-7 membered ring;
$R^9$ is selected from: hydrogen, $C_{1-6}$alkyl unsubstituted or substituted with 1-6 substituents selected from fluoro, $C_{1-3}$alkoxy, hydroxyl and —$COR^{11}$, $COR^{11}$, hydroxy and —O—$C_{1-6}$alkyl unsubstituted or substituted with 1-6 substituents selected from fluoro, $C_{1-3}$alkoxy, hydroxy, and —$COR^{11}$,
or $R^8$ and $R^9$ together are $C_{1-4}$alkyl or $C_{0-3}$alkyl-O—$C_{0-3}$ alkyl, forming a 3-6 membered ring;
$R^{10}$ is selected from: hydrogen, $C_{1-6}$alkyl unsubstituted or substituted with 1-6 fluoro, fluoro, —O—$C_{3-6}$cycloalkyl and —O—$C_{1-3}$alkyl unsubstituted or substituted with 1-6 fluoro,
or $R^8$ and $R^{10}$ together are $C_{2-3}$alkyl, forming a 5-6 membered ring, wherein said alkyl is unsubstituted or substituted with 1-3 substituents independently selected from halo, hydroxy, —$COR^{11}$, $C_{1-3}$alkyl, and $C_{1-3}$alkoxy,
or $R^8$ and $R^{10}$ together are $C_{1-2}$alkyl-O—$C_{1-2}$alkyl, forming a 6-8 membered ring, wherein said alkyl is unsubstituted or substituted with 1-3 substituents independently selected from halo, hydroxy, —$COR^{11}$, $C_{1-3}$alkyl, and $C_{1-3}$alkoxy, or R$^8$ and R$^{10}$ together are —O—C$_{1-2}$alkyl-O—, forming a 6-7 membered ring, wherein said alkyl is unsubstituted or substituted with 1-3 substituents independently selected from halo, hydroxy, —COR$^{11}$, C$_{1-3}$alkyl, and C$_{1-3}$alkoxy;

R$^{11}$ is independently selected from: hydroxy, hydrogen, C$_{1-6}$alkyl, —O—C$_{1-6}$alkyl, benzyl, phenyl and C$_{3-6}$cycloalkyl, wherein said alkyl, phenyl, benzyl and cycloalkyl are unsubstituted or substituted with 1-3 substituents independently selected from halo, hydroxy, C$_{1-3}$alkyl, C$_{1-3}$alkoxy, —CO$_2$H, —CO$_2$—C$_{1-6}$alkyl and trifluoromethyl;

R$^{12}$ is independently selected from: hydrogen, C$_{1-6}$alkyl, benzyl, phenyl and C$_{3-6}$cycloalkyl, wherein said alkyl, phenyl, benzyl and cycloalkyl are unsubstituted or substituted with 1-3 substituents independently selected from halo, hydroxy, C$_{1-3}$alkyl, C$_{1-3}$alkoxy, —CO$_2$H, —CO$_2$—C$_{1-6}$ alkyl trifluoromethyl;

R$^{13}$ is independently selected from: hydrogen, C$_{1-6}$alkyl, —O—C$_{1-6}$alkyl, benzyl, phenyl and C$_{3-6}$cycloalkyl, where said alkyl, phenyl, benzyl and cycloalkyl are unsubstituted or substituted with 1-3 substituents independently selected from halo, hydroxy, C$_{1-3}$alkyl, C$_{1-3}$alkoxy, —CO$_2$H, —CO$_2$—C$_{1-6}$alkyl and trifluoromethyl;

R$^{14}$ is independently selected from: hydroxy, C$_{1-6}$alkyl, —O—C$_{1-6}$alkyl, benzyl, phenyl and C$_{3-6}$cycloalkyl, wherein said alkyl, phenyl, benzyl and cycloalkyl are unsubstituted or substituted with 1-3 substituents independently selected from: halo, hydroxy, C$_{1-3}$alkyl, C$_{1-3}$alkoxy, —CO$_2$H, —CO$_2$—C$_{1-6}$alkyl and trifluoromethyl;

R$^{15}$ is selected from: hydrogen, —O—C$_{1-3}$alkyl unsubstituted or substituted with 1-6 fluoro, hydroxy, fluoro, C$_{1-3}$alkyl unsubstituted or substituted with 1-6 substituents independently selected from fluoro and hydroxy, —NR$^{12}$R$^{12}$, —COR$^{11}$, —CONR$^{12}$R$^{12}$, —NR$^{12}$COR$^{13}$, —OCONR$^{12}$R$^{12}$, —NR$^{12}$CONR$^{12}$R$^{12}$, -heterocycle, —CN, —NR$^{12}$—SO$_2$—NR$^{12}$R$^{12}$, —NR$^{12}$—SO$_2$—R$^{14}$, —SO$_2$—NR$^{12}$R$^{12}$ and =O where R$^{15}$ is connected to the ring via a double bond;

R$^{16}$ is selected from: hydrogen, fluoro and C$_{1-3}$alkyl unsubstituted or substituted with 1-6 substituents independently selected from fluoro and hydroxy, or R$^{16}$ is nothing when R$^{15}$ is connected to the ring through a double bond;

R$^{17}$ is selected from: C$_{1-6}$alkyl unsubstituted or substituted with 1-6 substituents selected from fluoro, C$_{1-3}$alkoxy, hydroxyl and —COR$^{11}$, fluoro, —O—C$_{1-3}$alkyl unsubstituted or substituted with 1-3 fluoro, C$_{3-6}$cycloalkyl, —O—C$_{3-6}$cycloalkyl, hydroxy, —COR$^{11}$, where R$^8$ and R$^{17}$ are not simultaneously methyl, or R$^{17}$ is nothing, if R$^8$ is connected via double bond (as in the case where R$^8$ is =O);

or R$^{17}$ and R$^8$ together form a bridge selected from —C$_{2-5}$alkyl-, —O—C$_{2-5}$alkyl-, —O—C$_{2-5}$alkyl-O—, —C$_{1-3}$alkyl-O—C$_{1-3}$alkyl-, wherein said alkyl groups are unsubstituted or substituted with 1-6 fluoro;

R$^{18}$ is selected from: hydrogen, C$_{1-6}$alkyl unsubstituted or substituted with 1-6 fluoro, fluoro, —O—C$_{3-6}$cycloalkyl and —O—C$_{1-3}$alkyl unsubstituted or substituted with 1-6 fluoro, n is selected from 0, 1 or 2, the dashed line represents an optional single bond;

and pharmaceutically acceptable salts thereof and individual diastereomers thereof.

Compounds of the present invention include compounds of formula Ia:

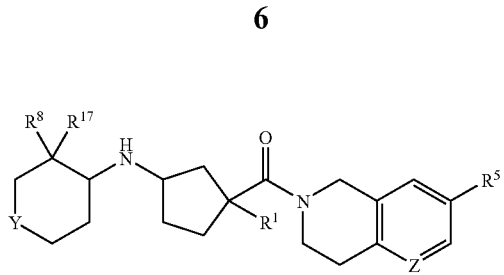

wherein R$^1$, R$^3$, R$^5$, R$^8$, R$^{17}$, Z, and Y are as described herein, and pharmaceutically acceptable salts and individual diastereomers thereof.

The present invention also includes compounds of formula Ib:

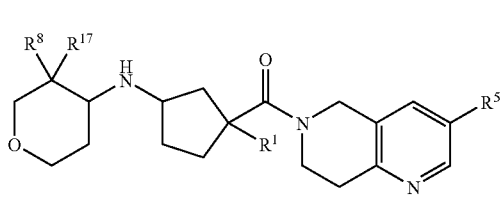

wherein R$^1$, R$^5$, R$^{17}$, and R$^8$ are described herein, and pharmaceutically acceptable salts and individual diastereomers thereof.

Embodiments of the present invention include those wherein Z is N.

Further embodiments of the present invention include those wherein Y is —CH$_2$— or —O—, and in particular those wherein Y is —O—.

Additional embodiments include those wherein R$^1$ is selected from: —C$_{1-6}$alkyl unsubstituted or substituted with 1-6 substituents independently selected from halo, hydroxy, —O—C$_{1-3}$alkyl, trifluoromethyl and —COR$^{11}$, —C$_{0-6}$alkyl-O—C$_{1-6}$alkyl-unsubstituted or substituted with 1-6 substituents independently selected from halo, trifluoromethyl and —COR$^{11}$, and —(C$_{3-5}$cycloalkyl)-(C$_{0-6}$alkyl) unsubstituted or substituted with 1-7 substituents independently selected from halo, hydroxy, —O—C$_{1-3}$alkyl, trifluoromethyl and —COR$^{11}$. In certain embodiments, R$^1$ is C$_{1-6}$alkyl unsubstituted or substituted with one or more of hydroxyl and 1-6 fluoro.

Embodiments of the present invention include those wherein when Z is C, R$^3$ is hydrogen, and those wherein when Z is N, R$^3$ is nothing.

In certain embodiments one or more of R$^2$, R$^4$, R$^6$, R$^7$, R$^9$, R$^{10}$, R$^{15}$, R$^{16}$ and R$^{18}$ is hydrogen.

Further, embodiments of the invention include those wherein R$^5$ is selected from: C$_{1-6}$alkyl substituted with 1-6 fluoro, —O—C$_{1-6}$alkyl substituted with 1-6 fluoro, chloro, bromo and phenyl. In particular R$^5$ may be selected from: trifluoromethyl, trifluoromethoxy, chloro, bromo and phenyl.

In certain embodiments of this invention R$^8$ is selected from C$_{1-3}$alkyl unsubstituted or substituted with 1-6 fluoro, —O—C$_{1-3}$alkyl, fluoro and hydroxy. In particular R$^8$ is selected from trifluoromethyl, methyl where R$^{17}$ is not methyl, methoxy, ethoxy, ethyl, fluoro and hydroxy.

Other embodiments include those wherein R$^{17}$ is selected from C$_{1-3}$alkyl unsubstituted or substituted with 1-6 fluoro, —O—C$_{1-3}$alkyl, fluoro and hydroxy. In particular R$^{17}$ is selected from trifluoromethyl, methyl where R$^8$ is not methyl, methoxy, ethoxy, ethyl, fluoro and hydroxy.

Further embodiments include those wherein $R^8$ and $R^{17}$ together are —O—CH$_2$CH$_2$—O— or —CH$_2$—CH$_2$—CH$_2$—CH$_2$—.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo.

As used herein, "alkyl" is intended to mean linear, branched and cyclic carbon structures having no double or triple bonds. $C_{1-8}$, as in $C_{1-8}$alkyl, is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. More broadly, $C_{a-b}$alkyl (where a and b represent whole numbers) is defined to identify the group as having a through b carbons in a linear or branched arrangement. $C_0$, as in $C_0$alkyl is defined to identify the presence of a direct covalent bond. "Cycloalkyl" is an alkyl, part or all of which forms a ring of three or more atoms.

The term "heterocycle" as used herein is intended to include the following groups:

benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The term "ring" is employed herein to refer to the formation or existence of a cyclic structure of any type, including free standing rings, fused rings, and bridges formed on existing rings. Rings may be non-aromatic or aromatic. Moreover, the existence or formation of a ring structure is at times herein disclosed wherein multiple substituents are defined "together", as in "... $R^8$ and $R^9$ together are $C_{1-4}$alkyl ...". In this case a ring is necessarily formed regardless of whether the term "ring" is employed.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfainic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media such as ether, ethyl acetate, ethanol, isopropanol, or acetonitrile are employed. Suitable salts are found, e.g. in Remington's Pharmaceutical Sciences, 17th ed., Mack Publishing Company, Easton, Pa., 1985, p. 1418.

Specific compounds within the present invention include a compound which selected from the group consisting of those compounds described in the Examples, and pharmaceutically acceptable salts thereof and individual diastereomers and enantiomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., J. Exp. Med., 177, 851-856 (1993) which may be readily adapted for measurement of CCR-2 binding.

Receptor affinity in a CCR-2 binding assay was determined by measuring inhibition of $^{125}$I-MCP-1 to the endogenous CCR-2 receptor on various cell types including monocytes, THP-1 cells, or after heterologous expression of the cloned receptor in eukaryotic cells. The cells were suspended in binding buffer (50 mM HEPES, pH 7.2, 5 mM MgCl$_2$, 1 mM CaCl$_2$, and 0.50% BSA or 0.5% human serum) and added to test compound or DMSO and $^{125}$I-MCP-1 at room temperature for 1 h to allow binding. The cells were then collected on GFB filters, washed with 25 mM BEPES buffer containing 500 mM NaCl and cell bound $^{125}$I-MCP-1 was quantified.

In a chemotaxis assay chemotaxis was performed using T cell depleted PBMC isolated from venous whole or leukophoresed blood and purified by Ficoll-Hypaque centrifugation followed by rosetting with neuraininidase-treated sheep erythrocytes. Once isolated, the cells were washed with HBSS containing 0.1 mg/ml BSA and suspended at 1×10$^7$ cells/ml. Cells were fluorescently labeled in the dark with 2

μM Calcien-AM (Molecular Probes), for 30 min at 37° C. Labeled cells were washed twice and suspended at 5×10$^6$ cells/ml in RPMI 1640 with L-glutamine (without phenol red) containing 0.1 mg/ml BSA. MCP-1 (Peprotech) at 10 ng/ml diluted in same medium or medium alone were added to the bottom wells (27 μl). Monocytes (150,000 cells) were added to the topside of the filter (30 μl) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HBSS containing 0.1 mg/ml BSA to remove cells that had not migrated into the filter. Spontaneous migration (chemokinesis) was determined in the absence of chemoattractant In particular, the compounds of the following examples had activity in binding to the CCR-2 receptor in the aforementioned assays, generally with an $IC_{50}$ of less than about 1 μM. Such a result is indicative of the intrinsic activity of the compounds in use as modulators of chemokine receptor activity.

Mammalian chemokine receptors provide a target for interfering with or promoting eosinophil and/or leukocyte function in a mammal, such as a human. Compounds which inhibit or promote chemokine receptor function, are particularly useful for modulating eosinophil and/or leukocyte function for therapeutic purposes. Accordingly, compounds which inhibit or promote chemokine receptor function would be useful in treating, preventing, ameliorating, controlling or reducing the risk of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In a certain embodiment, the disease or condition is one in which the actions of leukocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Inhibitors of chemokine receptor function may also be useful in the treatment and prevention of stroke (Hughes et al., *Journal of Cerebral Blood Flow& Metabolism*, 22:308-317, 2002; Takami et al., *Journal of Cerebral Blood Flow& Metabolism*, 22:780-784, 2002), obesity, type II diabetes, and neuropathic and inflammatory pain. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with modulators of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (Trichuriasis, Enterobiasis, Ascariasis, Hookworm, Strongyloidiasis, Trichinosis, filariasis), trematodes (flukes) (Schistosomiasis, Clonorchiasis), cestodes (tape worms) (Echinococcosis, Taeniasis saginata, Cysticercosis), visceral worms, visceral larva migraines (e.g., Toxocara), eosinophilic gastroenteritis (e.g., Anisaki sp., Phocanema sp.), and cutaneous larva migraines (Ancylostona braziliense, Ancylostoma caninum).

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in treating, preventing, ameliorating, controlling or reducing the risk of a wide variety of inflammatory and immunoregulatory disorders and diseases, allergic conditions, atopic conditions, as well as autoimmune pathologies. In a specific embodiment, the present invention is directed to the use of the subject compounds for treating, preventing, ameliorating, controlling or reducing the risk of autoimmune diseases, such as rheumatoid arthritis or psoriatic arthritis.

In another aspect, the instant invention may be used to evaluate putative specific agonists or antagonists of chemokine receptors, including CCR-2. Accordingly, the present invention is directed to the use of these compounds in the preparation and execution of screening assays for compounds that modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in treating, preventing, ameliorating, controlling or reducing the risk of infection by a retrovirus, in particular, herpes virus or the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a further aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, for instance a human being, male or female, in whom modulation of chemokine receptor activity is desired. "Modulation" as used herein is intended to encompass antagonism, agonism, partial antagonism, inverse agonism and/or partial agonism. In an aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

As used herein, the term "treatment" refers both to the treatment and to the prevention or prophylactic therapy of the aforementioned conditions.

Combined therapy to modulate chemokine receptor activity for thereby treating, preventing, ameliorating, controlling or reducing the risk of inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in treating, preventing, ameliorating, controlling or reducing the risk of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, embrel, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with CCR2 antagonists, such as the CCR2 antagonists compounds of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as brompheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3, CXCR-3 and CCR-5; (j) cholesterol lowering agents such as HMG-CoA reductase inhibitors (lovastatin, simvastatin and pravastatin, fluvastatin, atorvastatin, rosuvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) antidiabetic agents such as insulin, sulfonylureas, biguanides (metformin), α-glucosidase inhibitors (acarbose) and glitazones (troglitazone and pioglitazone); (1) preparations of interferon beta (interferon beta-1α, interferon beta-1β); (m) preparations of glatiramer acetate; (n) preparations of CTLA4Ig; (o) preparations of hydroxychloroquine, (p) Copaxone® and (q) other compounds such as 5-aminosalicylic acid and prodrugs thereof, antimetabolites such as azathioprine, 6-mercaptopurine and methotrexate, and cytotoxic cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In treating, preventing, ameliorating, controlling or reducing the risk of conditions which require chemokine receptor modulation an appropriate dosage level will generally be about 0.01 to 500 mg per kg patient body weight per day which can be administered in single or multiple doses. In certain embodiments the dosage level will be about 0.1 to about 250 mg/kg per day; or from about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, or 2.0 to 500, or 3.0 to 200, particularly 1, 5, 10, 15, 20, 25, 30, 50, 75, 100, 125, 150, 175, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, or once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are either commercially available or made by known procedures in the literature or as illustrated. The present invention further provides processes for the preparation of compounds of the formula I as defined above, which comprises many different sequences of assembling compounds of formula (II), formula (III), and formula (IV).

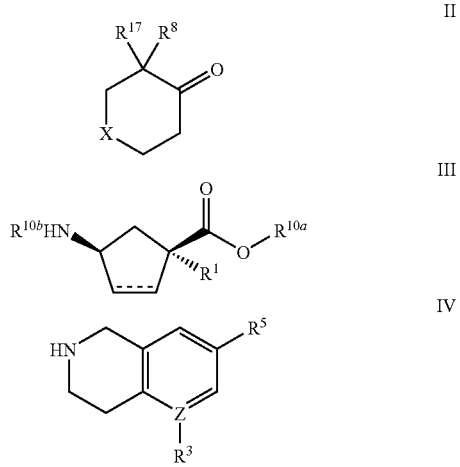

wherein $R^1$, $R^3$, $R^5$, $R^8$, $R^{17}$, Z, and X are defined as in formula I, and $R^{10a}$ represents either a hydrogen or an alkyl group such as methyl, ethyl, t-butyl, or benzyl which serves as a protecting group, $R^{10b}$ represent either hydrogen or an amine protecting group (Greene, T; Wuts, P. G. M. *Protective Groups in Organic Synthesis*, John Wiley & Sons, Inc., New York, N.Y. 1991) such as Boc or trifluoroacetate. The bond between the two carbon atoms where a dashed line is shown in formula III represents and optional bond as defined in formula I.

One general way of constructing target compounds I utilizing Intermediates of the formulas II, III, and IV is illustrated in Scheme 1. Coupling of the acid IIIa and the amine IV under standard amide bond formation reaction conditions such as PyBrop in the presence of a base such as N,N-diisopropylethylamine and a catalyst such as DMAP gives the intermediate 1-1. Removal of the Boc protecting group yields the amine 1-2. Reductive alkylation of 1-2 with ketones II in the presence of a borohydride such as sodium triacetoxyborohydride or sodium cyanoborohydride then provides the compound of formula Ia. Note that when $R^8$ or $R^{10}$ are other than hydrogen, a mixture of diastereomers (Eliel, E. E., Wilen, S. H., *Stereochemistry of Organic Compounds*, John Wiley & Sons, Inc., New York) results from the reductive amination step. These can be separated into their components by chromatography using normal phase, reverse phase or chiral columns, depending on the nature of the separation. Compound Ia can be further elaborated to the compound of the formula I by reductive alkylation with an aldehyde or by alkylation with, for example, an alkyl halide.

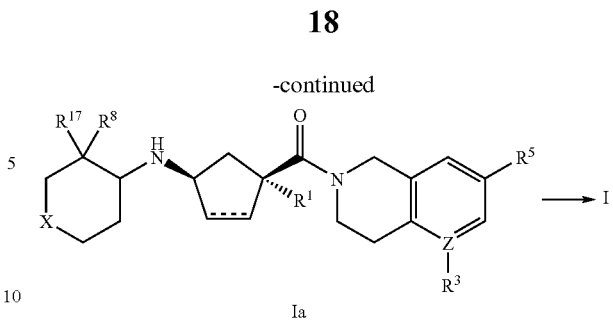

Ia

The cyclopentane core fragment III can be prepared in a number of ways. One of those is depicted in Scheme 2. According to Scheme 2, the commercially available homochiral lactam 2-1 is hydrogenated and the saturated 2-2 is treated with di-tert-butyl dicarbonate in the presence of a suitable catalyst, e.g. N,N-dimethylamino pyridine. A base catalyzed cleavage of the amide bond in the presence of a suitable alcohol $R^{10a}$—OH then provides the respective ester IIIa. The BOC-protecting group is removed, preferably with an acid such as HCl in a aprotic solvent, such as dioxane, to yield the amine IIIb in the form of a salt. When this amine is mixed with benzophenone imine, the respective Schiff base IIIc is formed, which can be obtained in pure form by simple filtration to remove ammonium chloride.

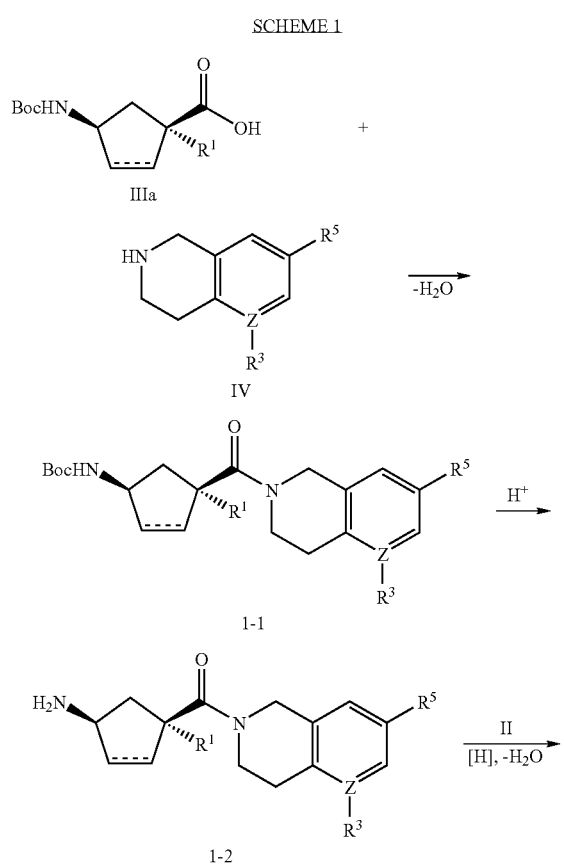

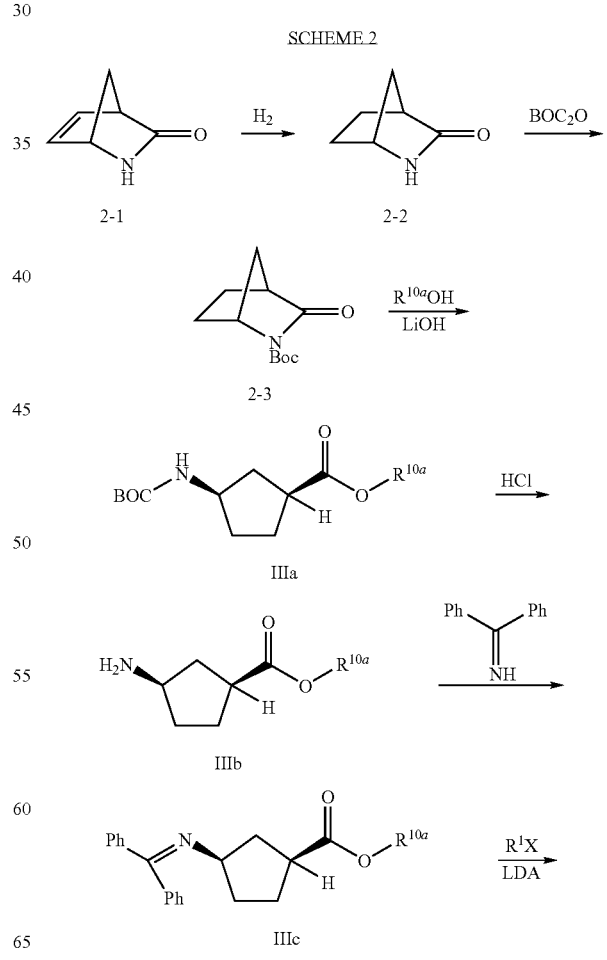

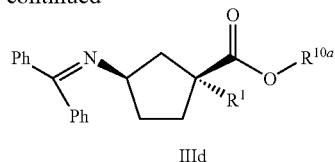

IIId

+

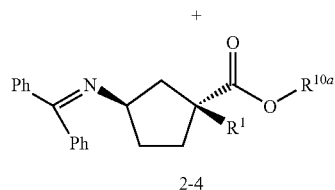

2-4

The enolate formed from ester IIIc with a strong base, such as LDA can be reacted with alkyl halides R¹—X, IIId, 2-4.

The desired cis diastereoisomer (IId) is then treated with an acid such as HCl to aid hydrolysis of the imine group and the resulting amino group IIIe can be suitably protected e.g. in a form of a tert-butoxycarbonyl amide (Scheme2B). The ester group present in intermediates IIIf can then be cleaved to give acid IIIg. The applied procedure depends on the nature of the ester: e.g. a benzyl ester can be cleaved by hydrogenolysis, a tert-butyl ester under acidic conditions and a alkyl ester can be hydrolyzed under either acidic or basic conditions.

SCHEME 2B

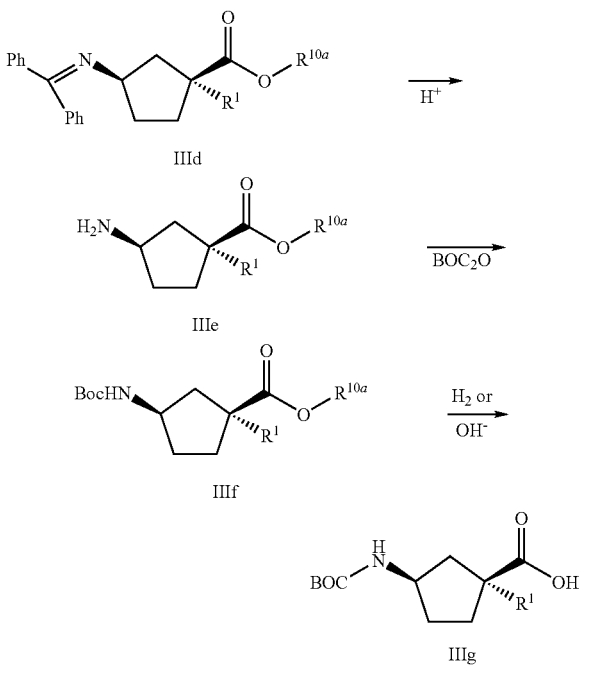

The amine fragment IV can be prepared purchased commercially or prepared in several ways, including in accordance to the literature methods.

The ketones II can be purchased commercially or prepared in several ways, including in accordance to literature methods.

In some cases the order of carrying out the foregoing reaction schemes may be varied to facilitate the reaction or to avoid unwanted reaction products.

The following are representative procedures for the preparation of the compounds used in the following Examples or which can be substituted for the compounds used in the following Examples which may not be commercially available.

INTERMEDIATE 1

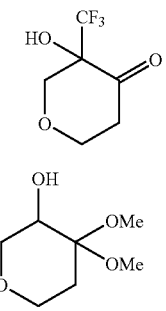

Step A

To a mixture of 5.6-dihydro-4-methoxy-2H-pyran (2.0 g, 18 mmol) in methanol (40 mL) at 0° C. was added m-CPBA (6.0 g, 35 mmol). After stirring for 10 min. at 0° C., the reaction mixture was allowed to warm to room temperature and stirred for 1 h. The solvent was removed under vacuum and the crude mixture was chromatographed on a silica column. Eluting with hexane: EtOAc (7:3) gave 2.8 g (95%) of the title compound. 1H NMR (CDCl₃, 500 MHz): 3.83 (m, 2H), 3.70 (m, 2H), 3.50 (m, 1H), 3.28 (s, 3H), 3.27 (s, 3H), 1.96 (m, 1H), 1.77 (m, 1H).

Step B

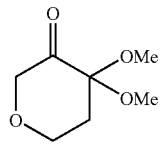

To a mixture of the acetal from Step A (2.8 g, 17 mmol) in dichloromethane (30 mL) was added 4 Å powdered molecular sieves (~5 g), 4-methylmorpholine N-oxide (5.0 g, 43 mmol) and finally TPAP (0.2 g). The resultant mixture was stirred vigorously for 3 h at which point the reaction was complete. It was filtered, evaporated, and purified by flash column chromatography on silica gel. Eluting with hexane: ether (1:4) gave the title compound (2.67 g, 96%).

Step C

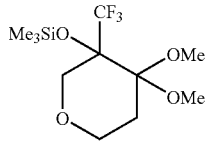

To the ketone from Step B (2.8 g, 18 mmol) in THF (20 mL) at 0° C. was added TBAF (28 mg) followed by neat trimethyl (trifluoromethyl)silane (4.0 g, 28 mmol). After stirring for 10 min. at 0° C., the reaction mixture was allowed to warm to room temperature and stirred for 12 h. THF was removed under vacuum and the crude passed through a silica gel column. Eluting with hexane: EtOAc (4:1) gave 4.1 g (77%) of the title compound.

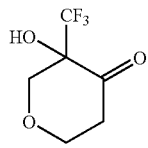

Step D

To the silylether from Step C (4.0 g, 13.3 mmol) at room temperature was added TFA (2.0 mL) and the mixture was stirred for 36 h. The TFA was removed under vacuum and the crude was purified by flash silica gel column chromatography. Eluting with hexane: ether (4:1) gave 1.5 g (65%) of the title compound. 1H NMR (CDCl$_3$, 500 MHz): 4.49 (m, 1H), 4.41 (m, 1H), 4.34 (br, 1H), 3.72 (m, 1H), 3.39 (m, 1H), 3.07 (m, 1H), 2.72 (m, 1H).

INTERMEDIATE 2

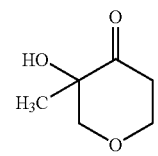

Step A

To a cooled (0 °C.) solution of oxalyl chloride (237 µL, 2.72 mmol) and DMSO (386 µL, 5.44 mmol) in dichloromethane (15 mL), under nitrogen, was added dropwise a prepared solution of the product from step A, intermediate 24 (220 mg, 1.36 mmol) in DCM (10 mL) via syringe. The mixture was stirred for 30 minutes at 0° C. and then triethylamine (1.52 mL, 10.9 mmol) was added via syringe and the resulting mixture was stirred overnight allowing to warm to room temperature. The solution was evaporated in vacuo and the residue was purified by preparative TLC (eluant: 60% ethyl acetate: 40% hexane) to afford the product (133 mg, 66%) as a yellow oil.

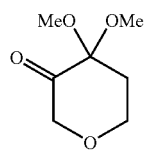

Step B

To a cooled (0° C.) solution of the product from Step A (50 mg, 0.31 mmol) in ether (3 mL), under nitrogen, was added dropwise methylmagnesium chloride (208 µL, 0.625 mmol) via syringe and the resulting mixture was stirred at 0° C. for 3 h. The reaction was quenched by the slow addition of a saturated solution of ammonium chloride (2 mL) and then the organic layer was separated. The aqueous layer was extracted with ether (3×5 mL) and the organics were combined, dried over anhydrous sodium sulfate, filtered, and evaporated under vacuum. The material was used without further purification for the next reaction. Yield was quantitative. $^1$H NMR (CDCl$_3$, 500 MHz): 3.78-3.74 (m, 1H), 3.45-3.38 (m, 2H), 3.42 (overlapped s, 3H), 3.31 (s, 3H), 3.26 (d, J=11 Hz, 1H), 1.93 (ddd, J=2.7, 5.3, 14.8 Hz, 1H), 1.72 (ddd, J=4.8, 11.9, 14.8 Hz, 1H), 1.34 (s, 3H).

Step C

A solution of product from Step B (50 mg, 0.31 mmol) in THF/water (1 mL/0.1 mL) was treated with concentrated hydrochloric acid (0.1 mL) and the resulting solution was stirred at room temperature for 1 h. The mixture was concentrated in vacuo to remove the THF and the aqueous layer was extracted with ether (6×5 mL). The organics were combined, dried over anhydrous sodium sulfate, filtered, and evaporated under reduced pressure to afford the product (7.5 mg, 18%) as a clear film. $^1$H NMR (CDCl$_3$, 500 MHz): 4.31 (ddd, J=3.2, 7.6, 11.2 Hz, 1H), 3.96 (dd, J=1.7, 11.0 Hz, 1H), 3.65 (ddd, J=3.0, 12.1 14.0 Hz, 1H), 3.36 (dd, J=1.5, 11.2 Hz, 1H), 2.91 (ddd, J=7.6, 11.9, 14.2 Hz, 1H), 2.50 (ddd, J=1.6, 2.9, 14.2 Hz, 1H), 1.51 (s, 3H).

INTERMEDIATE 3

Step A

A mixture of (1S)-(+)-2-azabicyclo[2.2.1]hept-5-en-3-one (10.3 g, 94.4 mmol) in EtOAc (200 mL) and 10% Pd/C (0.5 gm), was hydrogenated at room temperature under a hydrogen balloon. After 24 h the reaction mixture was filtered and evaporated leaving behind 10.4 g (100%) of a product that was taken in 250 mL methanol and HCl (12M, 6 mL). The resultant mixture was stirred at RT, until the reaction was complete (72 h). Evaporation of methanol followed by drying under high vacuum, yielded the title compound as an off white solid (16.0 g, 96%).

$^1$H NMR (D$_2$O, 500 MHz): 3.70 (s, 3H), 3.01 (m, 1H), 2.38 (m, 1H), 2.16-1.73 (m, 6H).

Step B

To a suspension of the intermediate from step A (10.2 g, 56.8 mmol) in dry dichloromethane (200 mL) was added benzophenone imine (10.2 g, 56.8 mmol) at room temperature and the resultant mixture was stirred for 24 h. The reaction mixture was filtered and the filtrate was evaporated, to leave behind a yellow oil that was triturated with ether (100 mL), filtered and evaporated. This operation was repeated twice to ensure that the product was free of ammonium chloride impurities. The resultant oil was thoroughly dried under vacuum to yield the title compound (18.03 g, >100%) and required no further purification. $^1$H NMR (CDCl$_3$, 500 MHz): 7.5-7.18 (m, 10H), 3.75 (m, 1H), 3.7 (s, 3H), 2.78 (m, 1H), 2.26-1.71 (m, 6H).

Step C

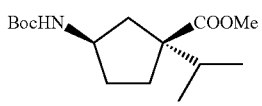

To a solution of LDA (prepared from diisopropylamine (7.7 g, 76.1 mmol) and n-butyllithium (30.4 mL, 2.5 M in hexane, 76 mmol) in THF (120 mL) at −78° C. was added the ester from Step B (18.0 g, 58.6 mmol). The resultant burgundy colored solution was stirred for 20 min. after which it was quenched with 2-iodopropane (14.9 gm, 88.0 mmol). The reaction mixture was gradually warmed over 3 h to 0° C. and this temperature was maintained for an additional 3 h. Reaction was quenched with water and extracted with EtOAc. The organic layer was washed with water, brine, dried (anhydrous magnesium sulfate) and concentrated to yield an oil. To the solution of the crude Schiff base (20.0 g) in THF (100 mL) was added HCl (5.0 mL, 12 M) and was allowed to stir at room temperature for 3 h. After the removal of all volatiles, the hydrochloride salt was taken up into dichloromethane (250 mL), and a saturated solution of sodium bicarbonate (250 mL) and di-tert-butyl dicarbonate (26.0 g, 1.4 Eq.) were added. The resultant mixture was vigorously stirred overnight at RT. The organic layer was separated and washed with water, brine, dried (anhydrous magnesium sulfate) and concentrated to yield an oil. Purification by flash column chromatography (eluent: hexane: EtOAc/19:1) gave the desired product (4.91 g, 30%). $^1$H NMR (500 MHz, CDCl$_3$): 4.79 (br, 1H), 4.01 (m, 1H), 3.71 (s, 3H), 2.18-1.60 (m, 6H), 1.44 (s, 9H), 0.87 (d, J=6.9 Hz, 3H), 0.86 (d, J=6.9 Hz, 3H).

Step D

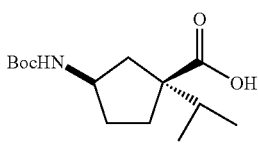

To a solution of the ester from the previous step (4.91 g, 17.2 mmol) in MeOH (100 mL) was added a solution of LiOH (3.6 g, 85 mmol) in water (20 mL) and THF (10 mL). The resultant mixture was heated at 80° C. until the reaction was complete (18 h). Methanol was removed in vacuo and the crude product was taken up with water/EtOAc (200 mL, 1:4) and cooled to 0° C. The acidity of the mixture was adjusted to pH 6. The EtOAc layer was separated, washed with water, brine, dried (anhydrous magnesium sulfate) and concentrated to yield an oil. Purification by flash column chromatography (eluent: hexane : EtOAc/1:1+2% AcOH) gave Intermediate 1 (3.9 g, 84%). $^1$H NMR (500 MHz, CDCl$_3$): 11.36 (br, 1H), 6.49 (br, 1H), 4.83 (m, 1H), 3.71 (s, 3H), 2.30-1.55 (m, 6H), 1.46 (s, 9H), 0.94 (d, J=6.9 Hz, 3H), 0.933 (d, J=6.9 Hz, 3H).

INTERMEDIATE 4

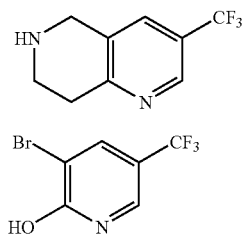

Step A

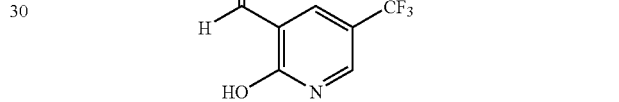

To a solution of 5-trifluoromethyl-2-pyridinal (51 g, 310 mmol) and sodium acetate (26.2 g, 319 mmol) in glacial acetic acid (200 mL) was added bromine (16.7 mL, 325 mmol) and the resulting mixture was heated at 80° C. for 2.5 h. The reaction was allow to cool to room temperature and then was evaporated under reduced pressure. The residue was neutralized with saturated NaHCO$_3$ solution and extracted with ethyl acetate (3×200 mL). The organics were combined, dried over MgSO$_4$, filtered, and evaporated in vacuo to yield 74.45 g (98%) of the crude product. $^1$H NMR (400 MHz, CDCl$_3$) δ 8.04 (d, J=2.6 Hz, 1H), 7.89 (m, 1H).

Step B

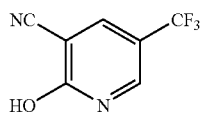

Under nitrogen, the substituted pyridine described in Step A, Intermediate 11 (48.8 g, 202 mmol) was added in small portions to a suspension of NaH (8.9 g, 220 mmol) in anhydrous tetrahydrofuran (500 mL). After complete addition of the intermediate, the reaction mixture was cooled to −78° C. and treated with tert-butyllithium (260 mL, 444 mmol) added dropwise via syringe. After stirring for 5 min, N,N-dimethylformamide (50 mL, 707 mmol) was added slowly to maintain the temperature below −50° C. The resulting mixture was then stirred for 10 h allowing it to warm to room temperature. The mixture was quenched with 2 N HCl and then diluted with ethyl acetate (1000 mL). The organic layer was separated, washed with brine, dried over MgSO4, and evaporated in vacuo. The desired product was precipitated out of ethyl acetate and hexanes and filtered to yield a light brown solid (28.55 g, 74%). $^1$H NMR (500 MHz, CD$_3$OD) δ 10.13 (s, 1H), 8.21 (s, 2H).

Step C

A mixture of the intermediate from Step B, Intermediate 11 (18 g, 95 mmol), sodium formate (7.1 g, 110 mmol), hydroxylamine hydrochloride (7.3 g, 110 mmol), and formic acid (150 mL) was stirred at room temperature for 2 h and then heated to reflux overnight. The reaction mixture was cooled and allowed to stand at room temperature for 7 days. The reaction was poured into water and extracted with ethyl acetate (3×). The combined organic layers were washed with water (2×), saturated NaHCO₃ and brine, dried over Na₂SO₄, filtered, and concentrated in vacuo to yield the desired product as a brown powder (17.84 g, 90%). ¹H NMR (400 MHz, CD₃OD) δ 8.37 (d, J=2.7 Hz, 1H), 8.19 (q, J=0.7 Hz, 0.3 Hz, 1H).

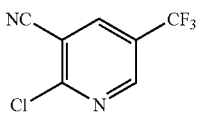

Step D

To a mixture of phosphorous oxychloride (13.4 mL, 144 mmol) and quinoline (8.7 mL, 73 mmol) was added the product from Step C, Intermediate 11, (24.6 g, 131 mmol) and the resulting mixture was heated to reflux for 3 h. The reaction was cooled to 100° C. before water (70 mL) was slowly added. The mixture was further cooled to room temperature and neutralized carefully with saturated NaHCO₃ solution. The aqueous layer was extracted with ethyl acetate (3×) and the organic layers were combined, dried over MgSO₄, filtered, and evaporated in vacuo. The crude product was purified by flash chromatography to afford (23.5 g, 87%) of the desired compound. ¹H NMR (500 MHz, CDCl₃) δ 8.88 (d, J=2.0 Hz, 1H), 8.26 (d, J=2.5 Hz, 1H).

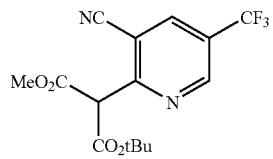

Step E

To a suspension of NaH (7.8 g, 200 mmol) in tetrahydrofuran (100 mL) under nitrogen was added dropwise a solution of tert-butyl methyl malonate (20 mL, 120 mmol) in anhydrous tetrahydrofuran (100 mL) via syringe. The reaction mixture was stirred for 0.5 h before a solution of the intermediate prepared in Step D, Intermediate 11 (20.1 g, 97.6 mmol) in tetrahydrofuran (200 mL) was added slowly via syringe. The reaction was stirred at room temperature overnight, then quenched with a saturated solution of NH₄Cl. The organic layer was separated and the aqueous layer was extracted with ethyl acetate (3×). The combined organic layers were washed with water (3×), dried over Na₂SO₄, filtered, and evaporated in vacuo. Flash chromatography afforded 31.76 g (95%) of the pure desired product. ¹H NMR (500 MHz, CDCl₃) δ 9.03 (d, J=1.5 Hz, 1H), 8.25 (d, J=2.0 Hz, 1H), 5.25 (s, 1H), 3.86 (s, 3H), 1.52 (s, 9H).

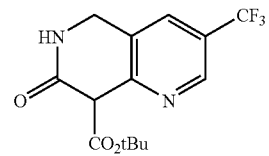

Step E

A suspension of Raney Ni (1 g) and the product from Step E, Intermediate 11 (18.2 g, 52.9 mmol) in ethanol (130 mL) was placed on a Parr apparatus and hydrogenated at 40 psi H₂ overnight. The suspension was filtered through celite and the filtrate was evaporated in vacuo to afford 16.35 g (98%) of the crude product. ¹H NMR (500 MHz, CDCl₃) δ 8.83 (s, 1H), 7.89 (s, 1H), 7.82 (s, 1H), 4.83 (d, J=16 Hz, 1H), 4.72 (s, 1H), 4.49 (d, J=16 Hz, 1H), 1.45 (s, 9H).

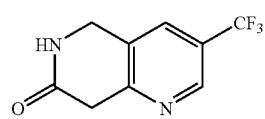

Step G

To the mixture of the product from Step F, Intermediate 11 (16 g, 51 mmol) in dichloromethane (60 mL) was added TFA (30 mL) and the resulting mixture was stirred at room temperature for 0.5 h. The solution was evaporated under reduced pressure and the residue was dissolved in dichloromethane. The mixture was neutralized by the slow addition of a solution of saturated sodium bicarbonate and the organic layer was removed. The aqueous layer was extracted with dichloromethane (4×) and the combined organic layers were dried over Na₂SO₄, filtered, and evaporated in vacuo to afford 10.42 g (95%) of the desired product. ¹H NMR (400 MHz, CDCl₃) δ 8.81 (s, 1H), 7.78 (s, 1H), 7.30 (s, 1H), 4.63 (s, 2H), 3.90 (s, 2H).

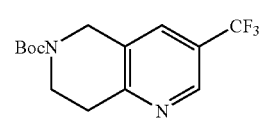

Step H

To a solution of the product from Step G, Intermediate 11 (18.0 g, 83.3 mmol) in tetrahydrofuran (50 mL) was added 1.0 M borane in tetrahydrofuran (417 mL, 420 mmol) and the resulting solution was stirred at room temperature overnight. The solution was evaporated under reduced pressure and the residue was treated with 1% HCl/methanol solution. The resutling mixture was heated at 50° C. overnight to breakdown the borane complex. Treatment with acidic methanol was repeated twice to insure that the borane complex was removed. A solution of this crude product (83.3 mmol, assuming 100% conversion) and diisopropylethylamine (43 mL, 250 mmol) in dichloromethane was treated with di-tert-butyl dicarbonate (36.4 g, 167 mmol) and the resulting mixture was stirred at room temperature overnight. The solution was washed with saturated sodium bicarbonate solution, water, and brine. The aqueous layers were combined and back-washed with dichloromethane (2×). The combined organic layers were then dried over Na₂SO₄, filtered, and evaporated to dryness. The crude product was purified by flash chromatography and MPLC to afford (11.89 g, 47%) as a yellow solid. ¹H NMR (500 MHz, CDCl₃) δ 8.69 (s, 1H), 7.66 (s, 1H), 4.67 (s, 2H), 3.79 (t, J=6.0 Hz, 2H), 3.08 (t, J=5.5 Hz, 2H), 1.51 (s, 9H).

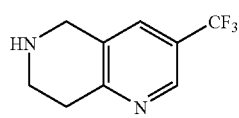

Step I

The product described in Step H, Intermediate 11 (11.89 g) was treated with a solution of 4 N HCl in dioxane. The solution was stirred at room temperature for 2 h and then evaporated in vacuo to afford Intermediate 12 (10.85 g, 99%) as a yellow powder. LC-MS for $C_9H_{10}F_3N_2$ calculated 202.07, found $[M+H]^+$203.0.

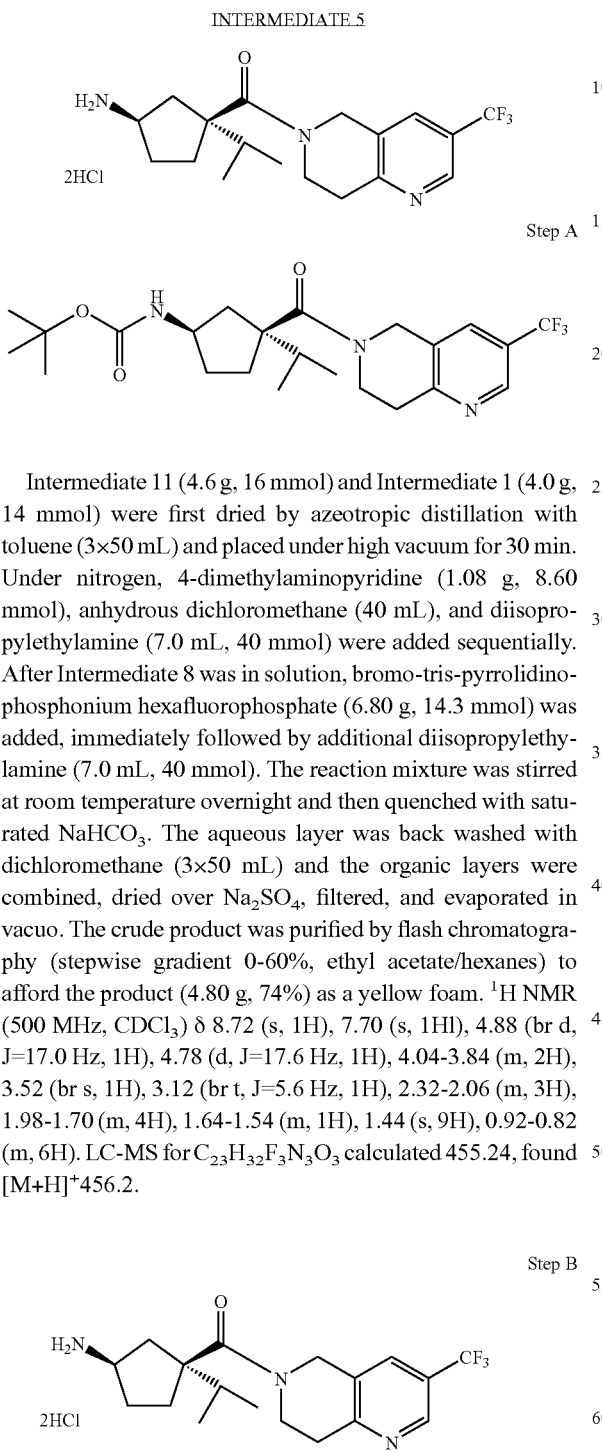

Intermediate 11 (4.6 g, 16 mmol) and Intermediate 1 (4.0 g, 14 mmol) were first dried by azeotropic distillation with toluene (3×50 mL) and placed under high vacuum for 30 min. Under nitrogen, 4-dimethylaminopyridine (1.08 g, 8.60 mmol), anhydrous dichloromethane (40 mL), and diisopropylethylamine (7.0 mL, 40 mmol) were added sequentially. After Intermediate 8 was in solution, bromo-tris-pyrrolidino-phosphonium hexafluorophosphate (6.80 g, 14.3 mmol) was added, immediately followed by additional diisopropylethylamine (7.0 mL, 40 mmol). The reaction mixture was stirred at room temperature overnight and then quenched with saturated NaHCO$_3$. The aqueous layer was back washed with dichloromethane (3×50 mL) and the organic layers were combined, dried over Na$_2$SO$_4$, filtered, and evaporated in vacuo. The crude product was purified by flash chromatography (stepwise gradient 0-60%, ethyl acetate/hexanes) to afford the product (4.80 g, 74%) as a yellow foam. $^1$H NMR (500 MHz, CDCl$_3$) δ 8.72 (s, 1H), 7.70 (s, 1Hl), 4.88 (br d, J=17.0 Hz, 1H), 4.78 (d, J=17.6 Hz, 1H), 4.04-3.84 (m, 2H), 3.52 (br s, 1H), 3.12 (br t, J=5.6 Hz, 1H), 2.32-2.06 (m, 3H), 1.98-1.70 (m, 4H), 1.64-1.54 (m, 1H), 1.44 (s, 9H), 0.92-0.82 (m, 6H). LC-MS for $C_{23}H_{32}F_3N_3O_3$ calculated 455.24, found $[M+H]^+$456.2.

The from Step B, Intermediate 12 (1.2 g, 2.6 mmol) was dissolved with 4 N HCl in dioxane (50 mL) and the resulting solution was stirred at room temperature for 1 h. The reaction was evaporated under vacuum to afford the product (904 mg, 97%) as a white powder. LC-MS calculated for $C_{18}H_{24}F_3N_3O$ is 355.20, found $[M+H]^+$356.2.

EXAMPLE 1

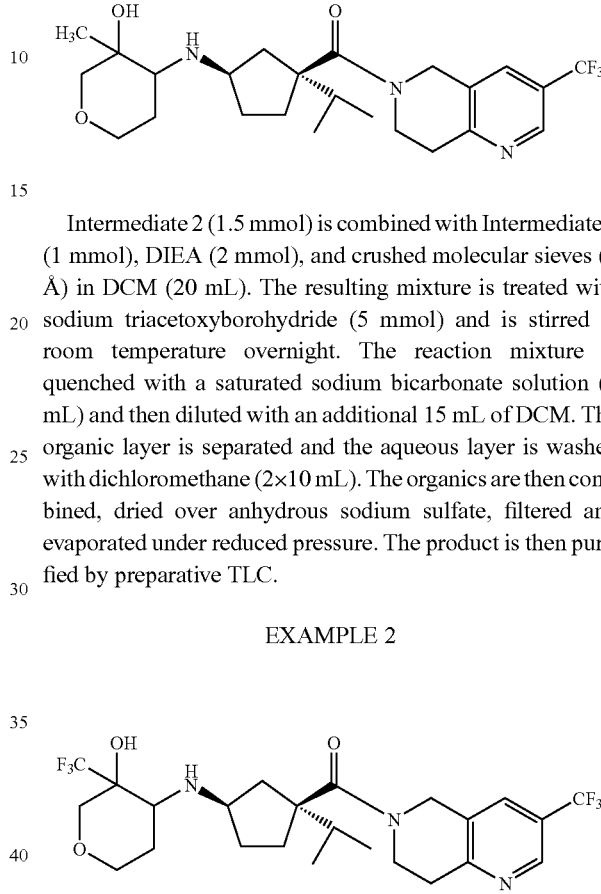

Intermediate 2 (1.5 mmol) is combined with Intermediate 5 (1 mmol), DIEA (2 mmol), and crushed molecular sieves (4 Å) in DCM (20 mL). The resulting mixture is treated with sodium triacetoxyborohydride (5 mmol) and is stirred at room temperature overnight. The reaction mixture is quenched with a saturated sodium bicarbonate solution (5 mL) and then diluted with an additional 15 mL of DCM. The organic layer is separated and the aqueous layer is washed with dichloromethane (2×10 mL). The organics are then combined, dried over anhydrous sodium sulfate, filtered and evaporated under reduced pressure. The product is then purified by preparative TLC.

EXAMPLE 2

Example 2 is prepared as described in Example 1, except that Intermediate 2 is replaced with Intermediate 1.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of Formula I:

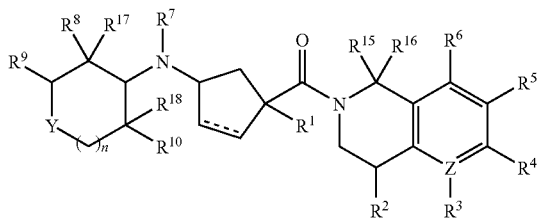

wherein:
Y is selected from: —O—, —NR$^{12}$—, —S—, —SO—, —SO$_2$—, —CR$^{12}$R$^{12}$—, —NSO$_2$R$^{14}$—, —NCOR$^{13}$—, —CR$^{12}$COR$^{11}$—, —CR$^{12}$OCOR$^{13}$—, and —CO—;

Z is C or N;

R$^1$ is selected from: hydrogen, —SO$_2$R$^{14}$, C$_{0-3}$alkyl-S(O)R$^{14}$, —SO$_2$NR$^{12}$R$^{12}$, —C$_{1-6}$alkyl, —C$_{0-6}$alkyl, —C$_{1-6}$alkyl, —C$_{0-6}$alkyl-S—C$_{1-6}$alkyl, —(C$_{0-6}$alkyl)-(C$_{3-7}$cycloalkyl)-(C$_{0-6}$alkyl), hydroxy, heterocycle, —CN, —NR$^{12}$R$^{12}$, —NR$^{12}$COR$^{13}$, —NR$^{12}$SO$_2$R$^{14}$, —COR$^{11}$, —CONR$^{12}$R$^{12}$, and phenyl, where said alkyl and said cycloalkyl are unsubstituted or substituted with 1-7 substituents independently selected from: halo, hydroxy, —O—C$_{1-3}$alkyl, trifluoromethyl, C$_{1-3}$alkyl, —O—C$_{1-3}$alkyl, —COR$^{11}$, —SO$_2$R$^{14}$, —NR$^{12}$COR$^{13}$, —NR$^{12}$SO$_2$R$^{14}$, -heterocycle, =O connected to R1 via a double bond, and —CN, where said phenyl and said heterocycle are unsubstituted or substituted with 1-3 substituents independently selected from: halo, hydroxy, COR$^{11}$, C$_{1-3}$alkyl, C$_{1-3}$alkoxy and trifluoromethyl;

R$^2$ is selected from: hydrogen, hydroxy, halo, C$_{1-3}$alkyl unsubstituted or substituted with 1-6 substituents independently selected from fluoro and hydroxy, —NR$^{12}$R$^{12}$, —COR$^{11}$, —CONR$^{12}$R$^{12}$, —NR$^{12}$COR$^{13}$, —OCONR$^{12}$R$^{12}$, —NR$^{12}$CONR$^{12}$R$^{12}$, -heterocycle, —CN, —NR$^{12}$—SO$_2$—NR$^{12}$R$^{12}$, —NR$^{12}$—SO$_2$—R$^{14}$, —SO$_2$—NR$^{12}$R$^{12}$ and =O, where R$^2$ is connected to the ring via a double bond;

R$^3$ is selected from: hydrogen, C$_{1-3}$alkyl, unsubstituted or substituted with 1-3 fluoro, —O—C$_{1-3}$alkyl unsubstituted or substituted with 1-3 fluoro, hydroxy, chloro, fluoro, bromo, phenyl, heterocycle, when Z is C, or R$^3$ is O or is absent, when Z is N;

R$^4$ is selected from: hydrogen, C$_{1-3}$alkyl, unsubstituted or substituted with 1-3 fluoro, —O—C$_{1-3}$alkyl optionally substituted with 1-3 fluoro, hydroxy, chloro, fluoro, bromo, phenyl and heterocycle;

R$^5$ is selected from: C$_{1-6}$alkyl unsubstituted or substituted with one or more of 1-6 fluoro and hydroxyl, —O—C$_{1-6}$alkyl unsubstituted or substituted with 1-6 fluoro, —CO—C$_{1-6}$alkyl unsubstituted or substituted with 1-6 fluoro, —S—C$_{1-6}$alkyl unsubstituted or substituted with 1-6 fluoro, -pyridyl unsubstituted or substituted with one or more halo, trifluoromethyl, C$_{1-4}$alkyl and COR$^{11}$, fluoro, chloro, bromo, —C$_{4-6}$cycloalkyl, —O—C$_{4-6}$cycloalkyl, phenyl unsubstituted or substituted with one or more of halo, trifluoromethyl, C$_{1-4}$alkyl and COR$^{11}$, —O-phenyl unsubstituted or substituted with one or more of halo, trifluoromethyl, C$_{1-4}$alkyl and COR$^{11}$, —C$_{3-6}$cycloalkyl unsubstituted or substituted with 1-6 fluoro, —O—C$_{3-6}$cycloalkyl unsubstituted or substituted with 1-6 fluoro, -heterocycle, —CN and —COR$^{11}$;

R$^6$ is selected from: hydrogen, C$_{1-3}$alkyl unsubstituted or substituted with 1-3 fluoro, —O—C$_{1-3}$alkyl unsubstituted or substituted with 1-3 fluoro, hydroxy, chloro, fluoro, bromo, phenyl and heterocycle;

R$^7$ is selected from: hydrogen and C$_{1-6}$alkyl unsubstituted or substituted with 1-3 substituents independently selected from halo, hydroxy, —CO$_2$H, —CO$_2$C$_{1-6}$alkyl and —O—C$_{1-3}$alkyl;

R$^8$ is selected from: C$_{1-6}$alkyl unsubstituted or substituted with 1-6 substituents where the substituents are chosen from the group: fluoro, C$_{1-3}$alkoxy, hydroxyl and —COR$^{11}$, fluoro, —O—C$_{1-3}$alkyl unsubstituted or substituted with 1-3 fluoro, C$_{3-6}$cycloalkyl, —O—C$_{3-6}$cycloalkyl, hydroxy, —COR$^{11}$, —OCOR$^{13}$ and =O, where the oxygen is connected to the ring via a double bond, or R$^7$ and R$^8$ together are C$_{2-4}$alkyl or C$_{0-2}$alkyl-O—C$_{1-3}$alkyl, forming a 5-7 membered ring;

R$^9$ is selected from: hydrogen, C$_{1-6}$alkyl unsubstituted or substituted with 1-6 substituents selected from fluoro, C$_{1-3}$alkoxy, hydroxyl and —COR$^{11}$, COR$^{11}$, hydroxy and —O—C$_{1-6}$alkyl unsubstituted or substituted with 1-6 substituents selected from fluoro, C$_{1-3}$alkoxy, hydroxy, and —COR$^{11}$, or R$^8$ and R$^9$ together are C$_{1-4}$alkyl or C$_{0-3}$alkyl-O—C$_{0-3}$alkyl, forming a 3-6 membered ring;

R$^{10}$ is selected from: hydrogen, C$_{1-6}$alkyl unsubstituted or substituted with 1-6 fluoro, fluoro, —O—C$_{3-6}$cycloalkyl and —O—C$_{1-3}$alkyl unsubstituted or substituted with 1-6 fluoro, or R$^8$ and R$^{10}$ together are C$_{2-3}$alkyl, forming a 5-6 membered ring, wherein said alkyl is unsubstituted or substituted with 1-3 substituents independently selected from halo, hydroxy, —COR$^{11}$, C$_{1-3}$alkyl, and C$_{1-3}$alkoxy, or R$^8$ and R$^{10}$ together are C$_{1-2}$alkyl-O—C$_{1-2}$alkyl, forming a 6-8 membered ring, wherein said alkyl is unsubstituted or substituted with 1-3 substituents independently selected from halo, hydroxy, —COR$^{11}$, C$_{1-3}$alkyl, and C$_{1-3}$alkoxy, or R$^8$ and R$^{10}$ together are —O—C$_{1-2}$alkyl-O—, forming a 6-7 membered ring, wherein said alkyl is unsubstituted or substituted with 1-3 substituents independently selected from halo, hydroxy, —COR$^{11}$, C$_{1-3}$alkyl, and C$_{1-3}$alkoxy;

R$^{11}$ is independently selected from: hydroxy, hydrogen, C$_{1-6}$ alkyl, —O—C$_{1-6}$alkyl, benzyl, phenyl and C$_{3-6}$ cycloalkyl, wherein said alkyl, phenyl, benzyl and cycloalkyl are unsubstituted or substituted with 1-3 substituents independently selected from halo, hydroxy, C$_{1-3}$alkyl, C$_{1-3}$alkoxy, —CO$_2$H, —CO$_2$—C$_{1-6}$ alkyl and trifluoromethyl;

R$^{12}$ is independently selected from: hydrogen, C$_{1-6}$ alkyl, benzyl, phenyl and C$_{3-6}$ cycloalkyl, wherein said alkyl, phenyl, benzyl and cycloalkyl are unsubstituted or substituted with 1-3 substituents independently selected from halo, hydroxy, C$_{1-3}$alkyl, C$_{1-3}$alkoxy, —CO$_2$H, —CO$_2$—C$_{1-6}$ alkyl and trifluoromethyl;

R$^{13}$ is independently selected from: hydrogen, C$_{1-6}$ alkyl, —O—C$_{1-6}$alkyl, benzyl, phenyl and C$_{3-6}$ cycloalkyl, where said alkyl, phenyl, benzyl and cycloalkyl are unsubstituted or substituted with 1-3 substituents independently selected from halo, hydroxy, C$_{1-3}$alkyl, C$_{1-3}$alkoxy, —CO$_2$H, —CO$_2$—C$_{1-6}$ alkyl and trifluoromethyl;

$R^{14}$ is independently selected from: hydroxy, $C_{1-6}$ alkyl, —O—$C_{1-6}$alkyl, benzyl, phenyl and $C_{3-6}$ cycloalkyl, wherein said alkyl, phenyl, benzyl and cycloalkyl are unsubstituted or substituted with 1-3 substituents independently selected from: halo, hydroxy, $C_{1-3}$alkyl, $C_{1-3}$alkoxy, —$CO_2H$, —$CO_2$—$C_{1-6}$ alkyl and trifluoromethyl;

$R^{15}$ is selected from: hydrogen, —O—$C_{1-3}$alkyl unsubstituted or substituted with 1-6 fluoro, hydroxy, fluoro, $C_{1-3}$alkyl unsubstituted or substituted with 1-6 substituents independently selected from fluoro and hydroxy, —$NR^{12}R^{12}$, —$COR^{11}$, —$CONR^{12}R^{12}$, —$NR^{12}COR^{13}$, —$OCONR^{12}R^{12}$, —$NR^{12}CONR^{12}R^{12}$, -heterocycle, —CN, —$NR^{12}$—$SO_2$—$NR^{12}R^{12}$, —$NR^{12}$—$SO_2$—$R^{14}$, —$SO_2$—$NR^{12}R^{12}$ and =O where $R^{15}$ is connected to the ring via a double bond;

$R^{16}$ is selected from: hydrogen, fluoro and $C_{1-3}$alkyl unsubstituted or substituted with 1-6 substituents independently selected from fluoro and hydroxy, or $R^{16}$ is nothing when $R^{15}$ is connected to the ring through a double bond;

$R^{17}$ is selected from: $C_{1-6}$alkyl unsubstituted or substituted with 1-6 substituents selected from fluoro, $C_{1-3}$alkoxy, hydroxyl and —$COR^{11}$, fluoro, —O—$C_{1-3}$alkyl unsubstituted or substituted with 1-3 fluoro, $C_{3-6}$ cycloalkyl, —O—$C_{3-6}$cycloalkyl, hydroxy, —$COR^{11}$, where $R^8$ and $R^{17}$ are not simultaneously methyl, or $R^{17}$ is nothing, if $R^8$ is connected via double bond;

or $R^{17}$ and $R^8$ together form a bridge selected from —$C_{2-5}$ alkyl-, —O—$C_{2-5}$alkyl-, —O—$C_{2-5}$alkyl-O—, —$C_{1-3}$ alkyl-O—$C_{1-3}$alkyl-, wherein said alkyl groups are unsubstituted or substituted with 1-6 fluoro;

$R^{18}$ is selected from: hydrogen, $C_{1-6}$alkyl unsubstituted or substituted with 1-6 fluoro, fluoro, —O—$C_{3-6}$cycloalkyl and —O—$C_{1-3}$alkyl unsubstituted or substituted with 1-6 fluoro n is selected from 0, 1 or 2; and the dashed line represents an optional single bond;

or a pharmaceutically acceptable salt thereof or an individual diastereomer thereof.

2. The compound of claim 1 having the formula Ia:

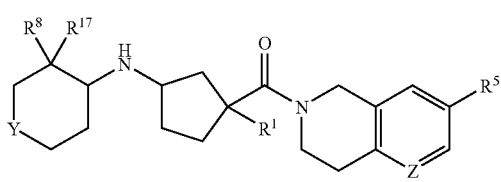

Ia or a pharmaceutically acceptable salt or individual diastereomer thereof.

3. The compound of claim 1 having the formula Ib:

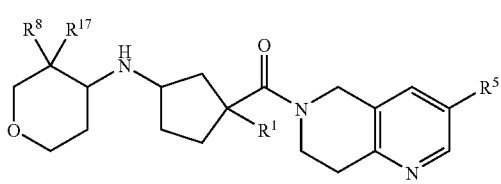

Ib or a pharmaceutically acceptable salt or individual diastereomer thereof.

4. The compound of claim 1 wherein Z is N.

5. The compound of claim 1 wherein Y is —$CH_2$— or —O—.

6. The compound of claim 1 wherein $R^1$ is selected from: —$C_{1-6}$alkyl unsubstituted or substituted with 1-6 substituents independently selected from halo, hydroxy, —O—$C_{-3}$alkyl, trifluoromethyl and —$COR^{11}$, —$C_{0-6}$alkyl-O—$C_{1-6}$alkyl- unsubstituted or substituted with 1-6 substituents independently selected from halo, trifluoromethyl and —$COR^{11}$, and —($C_{3-5}$cycloalkyl)-($C_{0-6}$alkyl) unsubstituted or substituted with 1-7 substituents independently selected from halo, hydroxy, —O—$C_{1-3}$alkyl, trifluoromethyl and —$COR^{11}$.

7. The compound of claim 1 wherein when Z is C, $R^3$ is hydrogen, and wherein when Z is N, $R^3$ is absent.

8. The compound of claim 1 wherein R5 is selected from: C1-6alkyl substituted with 1-6 fluoro, —O—$C_{1-6}$alkyl substituted with 1-6 fluoro, chloro, bromo and phenyl.

9. The compound of claim 1 wherein $R^8$ is selected from $C_{1-3}$alkyl unsubstituted or substituted with 1-6 fluoro, —O—$C_{1-3}$alkyl, fluoro and hydroxy.

10. The compound of claim 1 wherein $R^{17}$ is selected from $C_{1-3}$alkyl unsubstituted or substituted with 1-6 fluoro, —O—$C_{1-3}$alkyl, fluoro and hydroxy.

11. The compound of claim 1 wherein $R^8$ and $R^{17}$ together are —O—$CH_2CH_2$—O— or —$CH_2$—$CH_2$—$CH_2$—$CH_2$—.

12. A compound selected from:

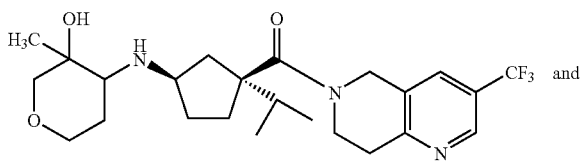

and

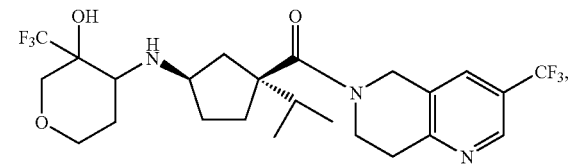

or a pharmaceutically acceptable salt thereof or an individual diastereomer or enantiomer thereof.

13. A pharmaceutical composition which comprises an inert carrier and the compound of claim 1.

14. A method of treating an inflammatory or immunoregulatory disorder or disease comprising the administration of a therapeutically effective amount of the compound of claim 1 to a patient in need of treatment wherein said disorder or disease is rheumatoid arthritis.

* * * * *